United States Patent [19]

Corey

[11] Patent Number: 5,132,321
[45] Date of Patent: Jul. 21, 1992

[54] ANTICOAGULANT/SURFACTANT RODENTICIDAL COMPOSITIONS AND METHOD

[75] Inventor: Garland G. Corey, Milltown, N.J.

[73] Assignee: Sterling Drug Inc., Rensselaer, N.Y.

[21] Appl. No.: 403,268

[22] Filed: Sep. 5, 1989

Related U.S. Application Data

[60] Division of Ser. No. 217,728, Jul. 11, 1988, Pat. No. 4,950,482, which is a continuation-in-part of Ser. No. 780,136, Sep. 25, 1985, abandoned.

[51] Int. Cl.$^5$ .................. A01N 43/16; A61K 31/35
[52] U.S. Cl. .................. 514/457; 424/84; 424/405; 523/122; 514/937; 252/106
[58] Field of Search ............... 424/84, 405; 523/122; 252/106; 514/937, 457

[56] References Cited

U.S. PATENT DOCUMENTS

| | | | |
|---|---|---|---|
| 2,687,365 | 7/1951 | Link | 424/410 |
| 3,544,677 | 12/1970 | Lapham | |
| 3,546,338 | 12/1970 | Engel et al. | |
| 3,574,832 | 4/1971 | Engel et al. | |
| 3,676,545 | 7/1972 | Saggers | |
| 3,941,882 | 3/1976 | O'Doherty | |
| 4,089,804 | 5/1978 | Falk | 252/356 |
| 4,178,388 | 12/1979 | Lechevin | |

FOREIGN PATENT DOCUMENTS

| | | | |
|---|---|---|---|
| 0002004 | 5/1979 | European Pat. Off. | |
| 7552244 | 9/1973 | Japan | 514/457 |
| 684234 | 6/1968 | South Africa | 514/457 |
| 1395955 | 5/1975 | United Kingdom | |
| 1479969 | 7/1977 | United Kingdom | |
| 1487811 | 10/1977 | United Kingdom | |

*Primary Examiner*—Lester L. Lee
*Assistant Examiner*—P. I. Curtis
*Attorney, Agent, or Firm*—John R. Everett

[57] ABSTRACT

Rodenticidal compositions comprising an anticoagulant type rodenticide in combination with a fluorosurfactant of the amphoteric, anionic or cationic type, optionally admixed with a cereal grain bait, and a method of killing rodents by oral administration of such compositions.

10 Claims, No Drawings

ANTICOAGULANT/SURFACTANT RODENTICIDAL COMPOSITIONS AND METHOD

RELATED APPLICATIONS

This application is a division of application Ser. No. 217,728, filed Jul. 11, 1988, now U.S. Pat. No. 4,950,980 which is a continuation-in-part of my prior, copending application Ser. No. 780,136, filed Sep. 25, 1985 now abandoned.

BACKGROUND OF THE INVENTION (a) Field of the Invention

This invention relates to rodenticidal compositions containing an anticoagulant agent and certain surface active agents.

(b) Information Disclosure Statement

The combination of anticoagulants, including anticoagulants conventionally used as rodenticides, with various surface active agents is known. However, in all known prior disclosures of such combinations, either the rationale for the combination is not revealed or the surfactant is indicated to be employed, for example, as a means of achieving improved wetting of bait with an aqueous solution of the particular rodenticidal agent, or as a conditioner or softening agent, or for the purpose of preventing agglomeration of the rodenticide. Furthermore the concept of combining an ionic fluorosurfactant with rodenticides of the anticoagulant type for the purpose of improving the rodenticidal properties thereof does not appear to be known or suggested by the prior art.

Thus Link U.S. Pat. 2,687,365 discloses the use of warfarin-treated cereal grain to which has been added other ingredients such as a polyhydric alcohol fatty acid "conditioner or softening agent", for example glyceryl oleo stearate.

Lapham et al. U.S. Pat. No. 3,544,677 discloses the use of anticoagulant halopyridinols as rodenticides which may be incorporated with "one or more of a plurality of additaments or innocuous ingestible adjuvants", including "surface active dispersing agents such as the liquid and solid emulsifying agents".

Engel et al. U.S. Pat. Nos. 3,546,338 and 3,574,832 disclose the combination of a solid dispersing agent, such as an anionic, cationic or nonionic dispersing agent, with heparin as an aid in improving the absorption of heparin through the alimentary canal.

Saggers et al. U.S. Pat. No. 3,676,545 discloses benzimidazole-containing rodenticidal compositions which it is stated can optionally contain a surface active agent to prevent agglomeration of the rodenticide powder.

O'Doherty U.S. Pat. No. 3,941,882 discloses imidazopyridine-containing rodenticidal compositions which can be combined with a "surface active dispersing agent". The latter, however, is neither exemplified nor is its purpose revealed.

Lechevin U.S. Pat. No. 4,178,388 discloses chlorophacinone containing rodenticidal compositions which may contain an "emulsifier", such as a "soluble metallic sulfonate or a polyoxyethylene ether". The emulsifier is not exemplified nor is its purpose revealed.

Japanese Patent Publication 75-52244 discloses a warfarin-treated rodenticidal bait which can optionally include an anionic surfactant. The purpose of the surfactant is to provide "high wetting power" so as to "promote permeation" of the warfarin throughout the grain bait.

South African Patent 68/4234 discloses slow release compositions of a variety of active ingredients, including warfarin sodium, from a water-in-oil emulsion which may contain a surfactant such as Arlacel, a nonionic surfactant.

SUMMARY OF THE INVENTION

It has been surprisingly found that combinations of anticoagulant type rodenticides with certain ionic fluorinated surfactants have a greater toxicity, as evidenced by a substantially lowered lethal dose ($LD_{50}$) and an increased percent mortality in rodents, than anticoagulant type rodenticides, such as warfarin, alone.

Accordingly, in a composition aspect, the invention relates to rodenticidal compositions for killing rats and mice containing an anticoagulant type rodenticide and a fluorosurfactant of the amphoteric, anionic or cationic types, said rodenticide and fluorosurfactant being present in a weight ratio from about 1:3 to about 1:30.

In a process aspect, the invention relates to a method of killing rodents which comprises orally administering thereto, or causing the rodents to ingest, a rodenticidal composition containing an anticoagulant type rodenticide and a fluorosurfactant of the amphoteric, anionic or cationic types, said rodenticide and fluorosurfactant being present in a weight ratio from about 1:3 to about 1:30.

DETAILED DESCRIPTION INCLUSIVE OF THE PREFERRED EMBODIMENTS

The rodenticidal compositions of the invention comprise a mixture containing an anticoagulant type rodenticide and an amphoteric, anionic or cationic fluorosurfactant. In a preferred aspect, the rodenticidal compositions comprise a conventional rodenticidal grain bait composed of a variety of cereal grains, such as wheat, barley, corn and oats, optionally containing flavoring agents such as sugar, molasses, salt and the like, admixed with the rodenticidal agent warfarin [3-(α-acetonylbenzyl)-4-hydroxycoumarin], and impregnated with an effective amount of the amphoteric, anionic or cationic fluorosurfactant.

The rodenticidal compositions containing the rodenticide and fluorosurfactant are prepared by admixing the two ingredients, the former typically as a mixture with starch and the latter typically in the form of a mixture in water and a water miscible alcohol, and drying the admixture before use.

The preferred rodenticidal compositions of the invention are prepared by admixing a cereal grain mixture, together with any flavoring agents, with a rodenticide/starch mixture, e.g. warfarin/starch, until the latter is homogeneously spread through the mass of grain bait. When warfarin is used as the rodenticide, the warfarin/starch mixture typically contains around 1% by weight of warfarin, and a sufficient amount of the warfarin/starch mixture is added to the cereal grain so as to provide around 0.06% by weight of warfarin in the final grain bait mixture. The warfarin treated grain bait mixture is then sprayed with the fluorosurfactant, preferably as an admixture with a liquid carrier, for example an alcohol such as ethyl alcohol. The weight ratio of rodenticide to fluorosurfactant is in the range from about 1:3 to 1:30, a preferred range being from about 1:5 to 1:15.

Preferred fluorosurfactants for the practice of the present invention are those manufactured and sold by E. I. Du Pont de Nemours and Company under their trademark ZONYL®, and particularly preferred fluorosurfactants of the ZONYL® group useful in the practice of the present invention are those sold under the Du Pont product designations FSB, FSJ, FSP, FSA and FSC, which have the following chemical structures:

FSB: $F(CF_2CF_2)_nCH_2CH_2N^{30}(CH_3)_2CH_2COO-$

FSJ: $F(CF_2CF_2)_nCH_2CH_2O\ PO(ONH_4)_2$

FSP: $[F(CF_2CF_2)_nCH_2CH_2O]_2PO(ONH_4)$

FSA: $F(CF_2CH_2)_nCH_2CH_2SCH_2CH_2CO_2Li$

FSC: $F(CF_2CF_2)_nCH_2CH_2SCH_2CH_2N^{30}(CH_3)_3\ CH_3SO_4+$ where n, in each instance, is an integer from 3 to 8. The properties of each of the latter are summarized in Table 1 below. Properties of a fluorosurfactant of the non-ionic type, ZONYL® FSN, having the chemical structure:

$F(CF_2CF_2)_nCH_2CH_2O(CH_2CH_2O)_xH$ which was tested and found to be ineffective in the practice of the present invention, are also included.

TABLE 2

| | | |
|---|---|---|
| Warfarin (1.162% on 98.838% starch) | 4.99 | (0.06 parts active) |
| Wheat | 19.96 | |
| Barley | 29.94 | |
| Oats | 29.94 | |
| Cornmeal | 9.98 | |
| Sugar | 4.99 | |
| Salt | 0.20 | |

Using the above-described basic bait formula (designated Formulation A), a series of test formulations, constituted as indicated in Table 3, was formulated by spraying a surfactant/ethanol mixture uniformly onto the dry bait with thorough mixing and then allowing the mixture to air dry. A mixture of the basic bait formulation sprayed with ethanol alone (Formulation B) served as an additional control. Formulation C, formulated with a non-fluorinated amphoteric surfactant (Miranol C2M, a cocoamphocarboxypropionic acid 50% actives), was included in order to compare the toxicity properties of a fluorinated and a non-fluorinated amphoteric surfactant. The surfactant type used in each formulation (amphoteric, anionic, cationic or nonionic) is indicated in the column headed "Surf. Type". The amounts are given in parts by weight. The ZONYL FSN, FSB and FSJ formulations each contained 40% actives, and the ZONYL FSC 50% actives. The weight of the actives in Formulation C was thus 0.715, in each of Formulations D-F 0.4 and in Formulation G 0.5. For comparative purposes, the ratios of warfarin:surfactant for the formulations containing such combinations are given in the last line as "Ratio".

TABLE 1

| | ZONYL Surfactant | | | | | |
|---|---|---|---|---|---|---|
| Property | FSB | FSJ | FSP | FSA | FSC | FSN |
| Type | Amphoteric | Anionic | Anionic | Anionic | Cationic | Nonionic |
| Physical Form | Liquid | Liquid | Liquid | Liquid | Liquid | Liquid |
| Diluent | i-PrOH/H$_2$O | i-PrOH/H$_2$O | i-PrOH/H$_2$O | i-PrOH/H$_2$O | i-PrOH/H$_2$O | i-PrOH/H$_2$O |
| % Solids | 40 | 40 | 35 | 50 | 50 | 40 |
| Density (lbs./gal.) | 8.8 | 9.8 | 9.6 | 9.8 | 9.7 | 8.8 |
| Flash Point, | 67 | 83 | 75 | 69 | 70 | 72 |
| °F. (a) | | | | | | |
| | 19° C. | 28° C. | 24° C. | 21° C. | 21° C. | 22° C. |
| Aqueous Surf. Tensions Dynes/cm., 25° C. | | | | | | |
| 0.01% Solids | 17 | 22 | 22 | 19 | 26 | 24 |
| 0.10% Solids | 17 | 20 | 19 | 18 | 18 | 23 |
| Stability 25° C. in: | | | | | | |
| 25% H$_2$SO$_4$ | Stable | Insol. | Insol. | Insol. | Stable | Stable |
| 37% HCl | Stable | Insol. | Insol. | Insol. | Stable | Stable |
| 70% HNO$_3$ | Stable | Insol. | Insol. | Insol. | Stable | Stable |
| 10% KOH | Stable | Stable | Stable | Stable | Stable | Stable |
| Solubility, 25° C. g. solids/100 g. soln. | | | | | | |
| H$_2$O | >2 | >2 | >2 | >2 | >2 | >2 |
| i-PrOH | >2 | 0.4 | 0.70 | 0.55 | >2 | >2 |
| 1:1 H$_2$O/i-PrOH | >2 | >2 | >2 | >2 | >2 | >2 |
| MeOH | >2 | >2 | >2 | >2 | >2 | >2 |
| Acetone | 1.25 | Sl. sol. | 0.15 | Insol. | >2 | >2 |
| Ethyl Acetate | Sl. sol. | Sl. sol. | Sl. sol. | Sl. sol. | 0.35 | >2 |
| Toluene | Sl. sol. | Insol. | Insol. | Sl. sol. | Insol. | 0.55 |
| n-Heptane | Insol. | Insol. | Insol. | Insol. | Insol. | 0.20 |
| THF | Insol. | Insol. | Insol. | Insol. | Sl. sol. | >2 |
| Methylchloroform | Insol. | Insol. | Insol. | Insol. | Sl. sol. | 0.50 |
| Acute Oral Toxicity | >25.0 | 11.0 | >17.0 | 1.5 | 1.0 | 22.3 |
| (Rats) (g./kg.) | (low tox.) | (low tox.) | (low tox.) | (sl. tox.) | (sl. tox.) | (low tox.) |

(a) Pensky Martens closed cup

For purposes of testing rodenticidal compositions in accordance with the present invention, a basic warfarin/cereal grain bait formulation, constituted as indicated in Table 2 below, was prepared by dry blending the ground cereal grain and warfarin/starch components together until a generally homogeneous mixture was obtained. The amounts are in parts by weight.

TABLE 3

| Surf. Type | | Formulation | | | | | | |
|---|---|---|---|---|---|---|---|---|
| | | A | B | C | D | E | F | G |
| Basic Bait | — | 100 | 100 | 100 | 100 | 100 | 100 | 100 |
| Ethanol | — | — | 19 | 19 | 19 | 19 | 19 | 19 |
| Miranol C2M | Ampho. | — | — | 1.43 | — | — | — | — |
| ZONYL FSN | Nonionic | — | — | — | 1 | — | — | — |
| ZONYL FSB | Ampho. | — | — | — | — | 1 | — | — |
| ZONYL FSJ | Anionic | — | — | — | — | — | 1 | — |
| ZONYL FSC | Cationic | — | — | — | — | — | — | 1 |
| Ratio | | — | — | 1:12 | 1:7 | 1:7 | 1:7 | 1:8 |

Each of these formulations was then tested for its toxicity against rats using FIFRA protocols according to the following procedure:

Male and female Wistar strain albino rats, approximately 6–8 weeks of age and weighing from 200–300 g., were used in the study. Test animals were maintained in cages on standard commercial rodent ration and water ad libitum for at least 6 days prior to initiation of the test procedure. An equal number of male and female animals, 5 of each, were used in each test group, and 24 hours prior to dosing, all rats were examined for respiratory difficulty, ocular or nasal lacrimation, dehydration, diarrhea and general thriftiness. The rats were fasted for approximately 18 hours pre-medication, then weighed and the weights used to calculate the dose of test composition per kilogram of body weight to be administered.

To determine the single dose mortality rate, each animal in each test group was administered an appropriate quantity of the test composition at a dose of 5 g./kg. by stainless steel intragastric feeding needle of sufficient bore to allow even passage of the composition. The rats were then returned to their cages, allowed food and water ad libitum and observed for mortality for a period of 14 days. The number of deaths in each group was determined and the results recorded as percent mortality for each group.

To determine the $LD_{50}$ for each composition, if an initial dose level of 5 g./kg. indicated that the $LD_{50}$ would be greater than 5 g./kg., no further testing was done. Otherwise dose ranging tests were carried out with groups of rats, equal numbers of each sex with 1 or 2 rats per sex per group being used at each of several dose levels with a wide spread between dose levels, the lowest dose level at which mortality occurred serving as a guide for choosing the first of several graded dose levels to be used. At least 3 dose levels were used, with additional levels used if necessary to produce test groups with mortality between 10% and 90% and to permit calculation of oral $LD_{50}$'s with a 95% confidence limit interval of 20% or less. The $LD_{50}$'s were calculated using the method of Litchfield and Wilcoxon, J. Pharmacol. Exptl. Therap. 96, 99–107 (1949).

The results obtained, expressed as the Lethal Dose$_{50}$ ($LD_{50}$) and the percent mortality at a single 5 g./kg. dose, are given in Table 4 below.

TABLE 4

| Formulation | 5 g./kg. % Mortality | $LD_{50}$ (g./kg.) |
|---|---|---|
| A | 20 | >5 |

TABLE 4-continued

| Formulation | 5 g./kg. % Mortality | $LD_{50}$ (g./kg.) |
|---|---|---|
| B | 30 | >5 |
| C | 30 | >5 |
| D | 30 | >5 |
| E | 100 | 2.48 |
| F | 80 | 3.10 |
| G | 60 | 2.85 |

These results show that the baits treated with amphoteric (ZONYL ® FSB, Formulation E), anionic (ZONYL ® FSJ, Formulation F) and cationic (ZONYL ® FSC, Formulation G) fluorosurfactants were toxic in the range from 2.5 to 3.1 g./kg. and showed a percent mortality at 5 g./kg. in the range from 60 to 100% and thus were more toxic than any of the basic bait formulation alone (Formulation A), the ethanol-treated bait formulation (Formulation B), the non-fluorinated amphoteric surfactant (Miranol C2M) treated bait formulation (Formulation C) or the nonionic fluorosurfactant (ZONYL ® FSN) treated bait formulation (Formulation D), the $LD_{50}$ value for each of the latter being in excess of 5 g./kg. and the percent mortality level at a 5 g./kg. dose for each being around 20 to 30%.

In order to determine the optimum levels of fluorosurfactant on the basic bait, a dose ranging study was carried out using three ZONYL ® FSB-treated bait formulations, constituted as indicated in Table 5, all formulations being prepared as above. An ethanol-treated bait served as control. As before, the ratio of warfarin:surfactant is given in the last line as "Ratio". Amounts are in parts by weight.

TABLE 5

| | Formulation | | | |
|---|---|---|---|---|
| | B | E-1 | E-2 | E-3 |
| Basic Bait | 100 | 100 | 100 | 100 |
| Ethanol | 19 | 19 | 19 | 19 |
| ZONYL FSB | — | 2.0 | 1.0 | 0.1 |
| Ratio | — | 1:13 | 1:7 | 1:0.7 |

The toxicities of each of these formulations, expressed as the $LD_{50}$ and as the percent mortality at the 5 g./kg. dose level and obtained as described above, are set forth in Table 6.

TABLE 6

| Formulation | 5 g./kg. % Mortality | $LD_{50}$ (g./kg.) |
|---|---|---|
| A | 20 | 5.8 |
| E-1 | 80 | 3.4 |
| E-2 | 50 | 3.7 |
| E-3 | 10 | >5.0 |

These data show that effective rodenticidal toxicity is obtained at levels of about 1 g. or greater of the fluorosurfactant per 100 g. of basic bait, i.e. at a weight ratio of warfarin:surfactant around 1:7 to 1:13 or greater. A weight ratio of approximately 1:1, as in Formulation E-3, is shown to offer no increase in toxicity relative to the basic bait.

From the foregoing it will be apparent to the person having ordinary skill in the art of rodenticides that other rodenticides of the anticoagulant type, for example dicoumarol [3,3'-methylenebis-(4-hydroxycoumarin)], bromodiolone [3-(4'-hydroxy-3'-coumarinyl) -3-phenyl-1-(4-bromo-4'-biphenylyl)propane -1-ol], diphenacoum [3-(3-p-biphenyl-1,2,3,4-tetrahydronaphth-1-yl)-4- hydroxycoumarin] and brodificou [3-(3-[4'-bromo-1-biphenyl]-1,2,3,4-tetrahydronaphth-1-yl)-4-hydroxycoumarin] may be combined with an appropriate surface active agent to prepare rodenticidal compositions having improved rodenticidal efficacy.

I claim:

1. A method of killing rodents which comprises orally administering to the rodents a rodenticidally effective amount of a rodenticidal composition containing an anticoagulant type rodenticide selected from the group consisting of warfarin, dicoumarol, bromodiolone, diphenacoum and brodificoum and a fluorosurfactant selected from the group consisting of $F(CF_2CF_2)_nCH_2CH_2N^+(CH_3)_2CH_2COO-$ $F(CF_2CH_2)_nCH_2CH_2OPO(ONH_4)_2$ $[F(CF_2CF_2)_nCH_2CH_2O]_2PO(ONH_4)$ $F(CF_2CF_2)_nCH_2CH_2SCH_2CO_2Li$ and $F(CF_2CF_2)_nCH_2CH_2SCH_2CH_2N^+(CH_3)_3 CH_3SO_4-$ where n, in each instance, is an integer from 3 to 8, said rodenticide and fluorosurfactant being present in a weight ratio from about 1:3 to about 1:30.

2. The method according to claim 1 wherein said composition comprises a cereal grain bait containing warfarin and said fluorosurfactant.

3. The method according to claim 2 wherein said warfarin and said fluorosurfactant are present in a weight ratio from 1:5 to 1:15.

4. The method according to claim 3 wherein the fluorosurfactant is a compound having the formula $F(CF_2CF_2)_nCH_2-CH_2N^+(CH_3)_2CH_2COO-$, where n has the meanings given above.

5. The method according to claim 3 wherein the fluorosurfactant is a compound having the formula $F(CF_2CF_2)_nCH_2-CH_2OPO(ONH_4)_2$, where n has the meanings given above.

6. The method according to claim 3 wherein the fluorosurfactant is a compound having the formula $F(CF_2CF_2)_nCH_2-CH_2SCH_2CH_2N^+(CH_{33} CH_3SO_4-$, where n has the meanings given above.

7. The method according to claim 4 wherein the weight ratio of said warfarin:fluorosurfactant is in the range from about 1:7 to 1:13.

8. The method according to claim 5 wherein the weight ratio of said warfarin:fluorosurfactant is in the range from about 1:7 to 1:13.

9. The method according to claim 6 wherein the weight ratio of said rodenticide:fluorosurfactant is in the range from about 1:7 to 1:13.

10. A method of killing rodents which comprises causing the rodents to ingest a rodenticidally effective amount of a rodenticidal composition comprising cereal grain bait containing an anticoagulant type rodenticide selected from the group consisting of warfarin, dicoumarol, bromodiolone, diphenacoum and brodificoum and a fluorosurfactant of the amphoteric, anionic or cationic type selected from the group consisting of $F(CF_2CF_2)_nCH_2CH_2N^+(Ch_3)_2CH_2COO-$ $F(CF_2CF_2)_nCH_2CH_2OPO(ONH_4)_2$ $[F(CF_2CF_2)_nCH_2CH_2O]_2PO(ONH_4)$ $F(CF_2CF_2)_nCH_2CH_2SCH_2CH_2CO_2Li$ and $F(CF_2CF_2)_nCH_2CH_2SCH_2CH_2N^+(CH_3)_3 CH_3SO_4-$ where n, in each instance, is an integer from 3 to 8, said rodenticide and fluorosurfactant being present in a weight ratio from about 1:3 to 1:30.

* * * * *